United States Patent [19]

Fournié et al.

[11] Patent Number: 4,497,640
[45] Date of Patent: Feb. 5, 1985

[54] PROCESS FOR THE DEHYDRATION OF GASES CONTAINING HYDROCARBONS

[75] Inventors: Francois J. C. Fournié, Paris; Christian J. A. Deleuze, Gradignan, both of France

[73] Assignees: Compagnie Francaise de Petroles; Commissariat a l'Energie Atomique, both of Paris, France

[21] Appl. No.: 576,826

[22] Filed: Feb. 3, 1984

[30] Foreign Application Priority Data

Feb. 4, 1983 [FR] France .................... 83 01815

[51] Int. Cl.³ .............................. B01D 53/22
[52] U.S. Cl. .......................... 55/16; 55/20; 55/21; 55/68
[58] Field of Search ........... 55/16, 20, 21, 30, 68

[56] References Cited

U.S. PATENT DOCUMENTS

| | | | |
|---|---|---|---|
| 3,274,750 | 9/1966 | Robb | 55/16 |
| 3,303,105 | 2/1967 | Konikoff et al. | 55/16 X |
| 3,510,387 | 5/1970 | Robb | 55/16 X |
| 3,675,391 | 7/1972 | Gallacher | 55/16 |
| 3,852,388 | 12/1974 | Kimura | 55/16 X |
| 4,119,417 | 10/1978 | Heki et al. | 55/16 X |
| 4,140,499 | 2/1979 | Ozaki et al. | 55/16 X |
| 4,180,388 | 12/1979 | Graham et al. | 55/158 X |
| 4,239,507 | 12/1980 | Benoit et al. | 55/16 |
| 4,264,338 | 4/1981 | Null | 55/16 |
| 4,268,279 | 5/1981 | Shindo et al. | 55/16 |

Primary Examiner—Robert Spitzer
Attorney, Agent, or Firm—Sughrue, Mion, Zinn, Macpeak and Seas

[57] ABSTRACT

In a process for the dehydration of gases by permeation through a membrane of selective permeability, the membrane comprises a bundle of hollow fibres based on polymers and open at both ends, the methane permeability of which is at least $10^{-5}$ cm$^3$/cm$^2$.s.cm Hg and the water/methane selectivity factor of which is greater than about 100. The gas to be dehydrated is supplied under pressure to a chamber through which the fibres extend and water-enriched gas is withdrawn from the interiors of the fibres. The fibres have internal diameters of between 0.1 mm and 0.5 mm, lengths of between 0.5 m and 3 m and thicknesses of between 0.05 mm and 0.3 mm, the thickness of the active layer of the membrane being less than 1 $\mu$m.

11 Claims, 9 Drawing Figures

PROCESS FOR THE DEHYDRATION OF GASES CONTAINING HYDROCARBONS

The present invention relates to the dehydration of gases containing hydrocarbons.

The following may be mentioned as gases containing hydrocarbons: natural gases, blanket gases located in layers lying above the oil layers in an oil field, associated gases obtained by the separation of a gas/oil mixture, and gases originating from a variety of sources such as oil refineries.

The presence of water in gases containing hydrocarbons is very troublesome because of the risks of solid hydrate formation and the risks of corrosion if these gases also contain carbon dioxide and/or hydrogen sulphide. It is necessary to reduce the water content to very small values if these gases are to be transported or conditioned for certain subsequent treatments such as liquefaction, or marketed.

In certain particular cases, it is possible to overcome the disadvantages of the presence of water in a gas by reducing the pressure of the gas and/or by heating the gas, but these processes are only applicable in the case of particular uses; for example, they are economically unacceptable where gases have to be transported over a long distance, and they are obviously unsuitable for marketing the gases and for complying with the specifications imposed on marketing.

The known processes of dehydration at the head include, in particular, dehydration by cooling, dehydration by contact with glycol, dehydration by adsorption onto silica gels, and dehydration over molecular sieves. All these processes require installations which are generally large and expensive, in particular if the gas is to be transported. Furthermore, the glycol dehydration units present problems of safety, weight and bulk, and the silica gel and molecular sieve systems can only be considered in very particular cases, because of their very high cost.

It is possible to consider the use of a passive system of permeation through a permeation membrane with a non-porous separating layer, which is capable of being automated, offers a high level of safety and is suitable for use in the sea, and which, when employed in a modular fashion, can easily be adapted to oil fields in development.

In fact, it has already been proposed to use such permeation systems for separating carbon dioxide and hydrogen sulphide from a gas by permeation. This technique is acceptable if indeed it is only required to separate off carbon dioxide or hydrogen sulphide. If, on the other hand, it is desired to dehydrate a gas, such systems result in bulky and expensive installations.

According to the invention there is provided a process for the dehydration of a gas containing hydrocarbons, using at least one permeator which comprises a feed compartment having an inlet and a permeation compartment separated from said feed compartment by a membrane of selective permeability, and comprising supplying a gas to be dehydrated under pressure to the inlet of said feed compartment, maintaining said permeation compartment at a lower pressure than said feed compartment, withdrawing a water-enriched gas from said permeation compartment and recovering a water-impoverished gas from said feed compartment, wherein said membrane comprises a bundle of hollow fibres based on polymers, which comprise an active layer and a substrate, having an internal diameter of between 0.1 mm and 0.5 mm, a length of between 0.5 m and 3 m and a thickness of between 0.05 mm and 0.3 mm, the thickness of the active layer alone being less than 1 $\mu$m, which have a methane permeability of at least $10^{-5}$ $cm^3/cm^2 \cdot s \cdot cm$ Hg and a water/methane selectivity factor of more than about 100, and which are open at both their longitudinal ends, the exterior of said hollow fibres being located in the feed compartment and the interior of said hollow fibres forming said permeation compartment.

The expression "permeability of a membrane to a compound in a gas" denotes the number of $cm^3$ of this compound which, when evaluated under normalised temperature and pressure conditions, pass through a 1 $cm^2$ area of this membrane in 1 second, under a pressure difference of 1 cm of mercury between the feed compartment and the permeation compartment. The methane permeability will be denoted by $P/CH_4$.

The ratio of the water permeability, $P/H_2O$, to the methane permeability, $P/CH_4$, of this membrane, under actual use conditions, is called the water/methane selectivity factor.

It should be noted that the methane permeability and the water/methane selectivity factor of a membrane are actual parameters of the shaped membrane and can be measured on the latter. These characteristic parameters of a membrane are different from the intrinsic characteristics of the material used, measured on this material in bulk; the conversion of the material to the membrane in fact requires the production of very thin layers which no longer have the intrinsic properties of the material. In particular, it is very difficult to preserve a high selectivity factor. An unexpected observation made in the course of the studies which led to the present invention was that excellent performance characteristics were obtained with membranes having relatively low water selectivity factors and that the performance characteristics were not substantially improved by using membranes of greater selectivity.

According to the invention it is therefore possible to choose a membrane which is very permeable to methane, while at the same time accepting only a moderate water selectivity, whereas the emphasis hitherto has always been placed on the need for a high selectivity of the membranes to the gaseous compound which it is desired to remove, compared with the selectivity to the other constituents of the gaseous mixture to be treated, and especially to the other constituent which permeates through the membranes most rapidly. It will be noted in this respect that, of the constituents other than water in a gaseous mixture containing hydrocarbons, methane is not generally one of those constituents which permeate most rapidly through a membrane; for example, a cellulose acetate membrane can be eight times more permeable to carbon dioxide, twenty-seven times more permeable to hydrogen and twenty-four times more permeable to helium than to methane.

The low water selectivity of the membrane which may be used according to the invention makes it easier to produce on account of the fact that the performance characteristics of the membranes can be very inferior to those which could be expected of their constituent material; this is because of the defects which appear during the manufacture of the thin films forming the active part of these membranes.

Complicated techniques for the manufacture of membranes have been devised for avoiding or masking these defects. In contrast, in the case of the present invention, it can be possible to tolerate these defects and to accept a reduction in the selectivity of the membrane ready for use, compared with the intrinsic selectivity of its constituent material.

The values of the lower limits given for the methane permeability and for the water/methane selectivity are values below which a sudden deterioration in the performance characteristics was observed, together with a consequent rapid increase in the membrane area required to treat a given flow rate of gas so as to reduce its water content to a preset value, as will be clearly shown below with the aid of a particular example.

Preferably, the water/methane selectivity factor of the membrane chosen according to the invention is between about 200 and 400 and the methane permeability of the membrane is of the order of $10^{-4}$ cm$^3$/cm$^2$.s.cm Hg.

It was found that the effect of a double exit from the hollow fibres was very important with high membrane permeabilities and the geometrical characteristics of the hollow fibres according to the invention, and made it possible considerably to reduce the area of membrane to be installed.

The characteristics of the process (geometry of the hollow fibres and their permeability and selectivity) are particularly well suited to high flow rates of gas to be treated, for example flow rates of more than $10^6$ Nm$^3$/day.

The high permeability of the membrane makes it possible to treat high flow rates of gas per square meter of membrane.

In certain cases part of the water-impoverished gas from the permeator may be recycled to reduce the water content of the gas entering the permeator and increase the life of the membrane.

A set of two permeators as described above may be arranged in cascade, the downstream permeator receiving the water-impoverished gas which leaves the upstram permeator, and the water-enriched gas which leaves the downstream permeator being returned to the inlet of the upstream permeator.

Alternatively a set of first and second permeators as described above may be arranged in such a way that the second permeator receives the water-enriched gas leaving the first permeator and the water-impoverished gas leaving the second permeator is returned to the inlet of the first permeator.

These assemblies of two permeators in cascade may be used, for example, to obtain very low water contents and/or to improve the recovery of the treated gas.

Embodiments according to the invention will now be described, by way of example only, with reference to the accompanying drawings.

Figure 1:
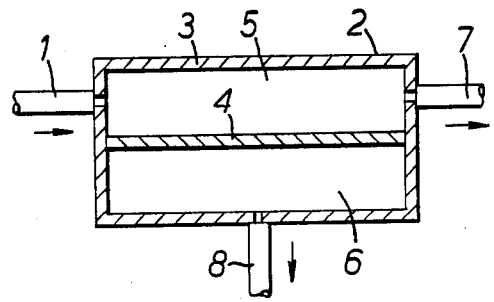
FIG. 1 is a diagrammatic view of a permeator according to the present invention.

In FIG. 1, a gas to be dehydrated is supplied through an inlet pipe 1 to a permeator 2 represented diagrammatically by an envelope 3, the internal volume of which is separated by a membrane 4 into a feed compartment 5 at relatively high pressure and a permeation compartment 6 at a relatively low pressure. An outlet pipe 7 makes it possible to withdraw gas which has become impoverished in water by flowing along the membrane 4, while an outlet pipe 8 makes it possible to discard or recover gas which has become enriched in water by passing through the membrane 4.

The pressure of the gas arriving through the pipe 1 is, for example, between 30 and 100 bar. This pressure could be as little as about 10 bar or could be as much as 150 bar or more. The temperature of the gas in the pipe 1 must be approximately between 0 and 100 degrees Centigrade if the membrane 4 is an organic membrane. The pressure in the compartment 6 can be adjusted by a valve (not shown), for example to a value close to atmospheric pressure. This valve can be fitted to the pipe 8.

The gas arriving through the pipe 1 contains methane and heavier hydrocarbons which are gaseous under the thermodynamic conditions of the gas in the pipe 1, together, if appropriate, with carbon dioxide and hydrogen sulphide, in widely varying proportions, and other constituents or impurities. The water content of this gas can vary very widely, ranging from a few parts per million to saturation of the gas with water. Depending on the particular case, the desired dehydration must convert a high content to a content of a few parts per million or simply effect a slight adjustment in the initial water content of the gas.

The membrane 4 is chosen, other than for its compatibility with water and hydrocarbons, essentially to have a good methane permeability, a moderate water/methane selectivity being accepted and no attention being paid to the permeability to the other constituents of the mixture to be treated. This makes it possible, in particular, to use a membrane having the methane permeability characteristics and water/methane selectivity characteristics defined above, irrespective of the hydrocarbon gas to be dehydrated.

As an example, a methane permeability of $10^{-4}$ cm$^3$/cm$^2$.s.cm Hg and a water/methane selectivity factor of 200 is chosen.

The membrane is produced starting from a material consisting of a single substance or a mixture of compounds such as polymers, which, in bulk, is moderately selective to water, and it is shaped by the known processes to give a membrane in the form of hollow fibres.

Preferably, at least one of the constituents of the chosen material is taken from the group of materials which can contain chains or branches of hydrophilic tendency, such as cellulose acetate, polyamides sold under the trade name NYLON, carboxymethylcellulose, ethylcellulose, methylcellulose and the like. The selective material can be used mounted on a substrate, which gives it a better mechanical strength, or can be used in the production of a composite membrane of asymmetric structure. The selective layer is made with the smallest possible thickness which gives a good permeability, and this is achieved all the more easily because there is a wide choice of selective materials, it being sufficient to have a moderate water selectivity. It is therefore relatively easy to obtain the permeability defined above.

Figure 2:
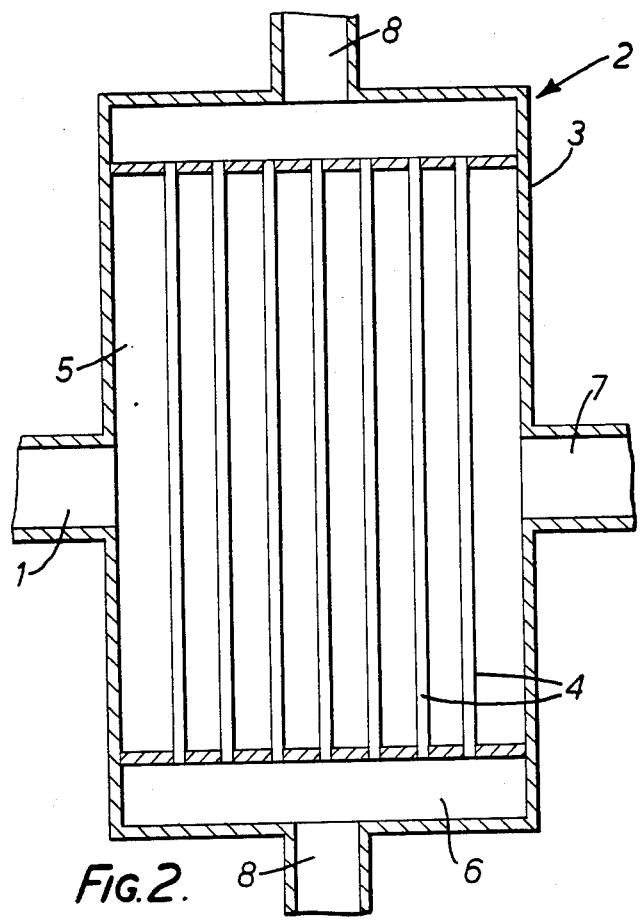
FIG. 2 is a diagrammatic view of a particular construction of the permeator of FIG. 1.

The membrane 4 has been shown very diagrammatically in FIG. 1. In reality, it consists of a bundle of hollow fibres which are fed in parallel, from the outside of the fibres, with gas to be dehydrated, the gas then passing selectively through the membranes from the outside of the fibres to the inside. The water-enriched gas is collected from the inside of these fibres and leaves through the two longitudinal ends of each fibre, as shown in FIG. 2.

The compartment 5 thus comprises all the spaces between hollow fibres, while the compartment 6 comprises all the spaces inside the hollow fibres.

In fact, as the process is applied to a high flow rate of permeated gas, attention must be paid to the pressure losses in the compartment 6. It is therefore necessary to optimise the permeator 2: the shape, dimensions and arrangement of the compartments 5 and 6 and of the membranes 4, and the process parameters such as pressures, temperatures and the like, and to endeavour to maintain the highest possible ratio of high pressure to low pressure throughout the permeator 2.

As the membrane 4 enables water vapour to permeate more rapidly than the other components of the gas arriving through the pipe 1, this gas becomes impoverished in water when flowing through the enclosure 5 along the membrane 4, and leaves through the pipe 7 with a reduced water content. Conversely, the gas which has passed through the membrane 4 is richer in water than the gas arriving through the pipe 1; thus, a water-enriched gas is withdrawn through the pipe 8.

Depending on the reduction which it is desired to obtain in the water content, and by using a membrane such as that described in the example which has just been given, it is possible to treat a gas flow rate of ten million $Nm^3$/day with a membrane area of between 500 and 5000 $m^2$.

For example, a natural gas saturated with water at 50 bar and 20° C. can be dehydrated, at a flow rate of gas to be treated of 10 million $Nm^3$/day, with a membrane according to the invention, adapted for dehydration, having the characteristics $P/CH_4 = 10^{-4}$ $cm^3/cm^2.s.cm$ Hg and $H_2O/CH_4$ selectivity factor = 200, and having an area of 1600 $m^2$.

By contrast, if it were desired to dehydrate the gas in this example by means of a membrane having a $CH_4$ permeability of 0.5 $cm^3/cm^2.s.cm$ Hg and an $H_2O/CH_4$ selectivity factor of 1000, 23,000 $m^2$ of membrane would be required for the same flow rate, which shows the advantage of a membrane specific for dehydration, possessing a high permeability and a moderate selectivity.

An example of a membrane suitable for carrying out the process according to the invention can be produced, in particular, from ethylcellulose, which is a hydrophilic material having the following intrinsic characteristics: methane permeability = $6 \times 10^{-10}$ $cm^3/cm^2.s.cm$ Hg and water/methane selectivity factor = 4000. A thin active layer of ethylcellulose was formed by a conventional method, with a thickness of 0.3 μm in one particular case, and this was deposited on a microporous substrate in order to give it mechanical strength. Without masking the defects, this gave a membrane having the following characteristics in this particular case: methane permeability = $5 \times 10^{-5}$ $cm^3/cm^2.s.cm$ Hg and water/methane selectivity factor = 140.

The fact that the selectivity factor has fallen to 140 where the intrinsic selectivity factor of the material used was 4000 shows that this membrane has defects, but these defects do not detract from its efficiency in the dehydration of hydrocarbon gases.

By way of example, for a gas to be treated having the following percentage molar composition: $CH_4 = 81.7$; $C_2H_6 = 5.3$; $C_3H_8 = 2.2$; $C_4H_{10} = 1.4$; $C_5H_{12} = 0.7$; $C_6H_{14} = 0.8$; $N_2 = 0.2$; $CO_2 = 3.9$; $H_2S = 3.2$; $H_2O = 0.5$, at a temperature of 60° C. and at a pressure of 70 bar and flowing at a rate of 280,000 $Nm^3$/hour, an experiment was carried out to find the membrane area required to lower the water content of the gas to 145 ppm with a membrane, produced, for example, in the manner just described, having a water/methane selectivity factor of 200 and existing in the form of hollow fibres with an external diameter of 0.5 mm and an internal diameter of 0.3 mm.

It was thus found that, with fibres having a length of 1 m and a methane permeability of $10^{-4}$, $10^{-5}$ and $10^{-6}$ $cm^3/cm^2.s.cm$ Hg, it is necessary to have a respective membrane area of 2100 $m^2$, 13,200 $m^2$ and 129,800 $m^2$ if the fibres are closed at one end, and of 1300 $m^2$, 11,200 $m^2$ and 111,000 $m^2$ if the fibres are open at both ends.

With fibres having a length of 2 m, the areas found under the same conditions are 4200 $m^2$, 14,500 $m^2$ and 131,600 $m^2$ if the fibres are closed at one end, and 1900 $m^2$, 11,500 $m^2$ and 111,500 $m^2$ if the fibres are open at both ends.

It is thus seen that, for example, with a methane permeability of $10^{-4}$ $cm^3/cm^2.s.cm$ Hg and fibres closed at one end, it is necessary to have twice the membrane area with fibres having a length of 2 m (4200 $m^2$) than with fibres having a length of 1 m (2100 $m^2$) in order to perform the same dehydration operation. The additional membrane area used with fibres having a length of 2 m is therefore totally ineffective.

Figure 3:
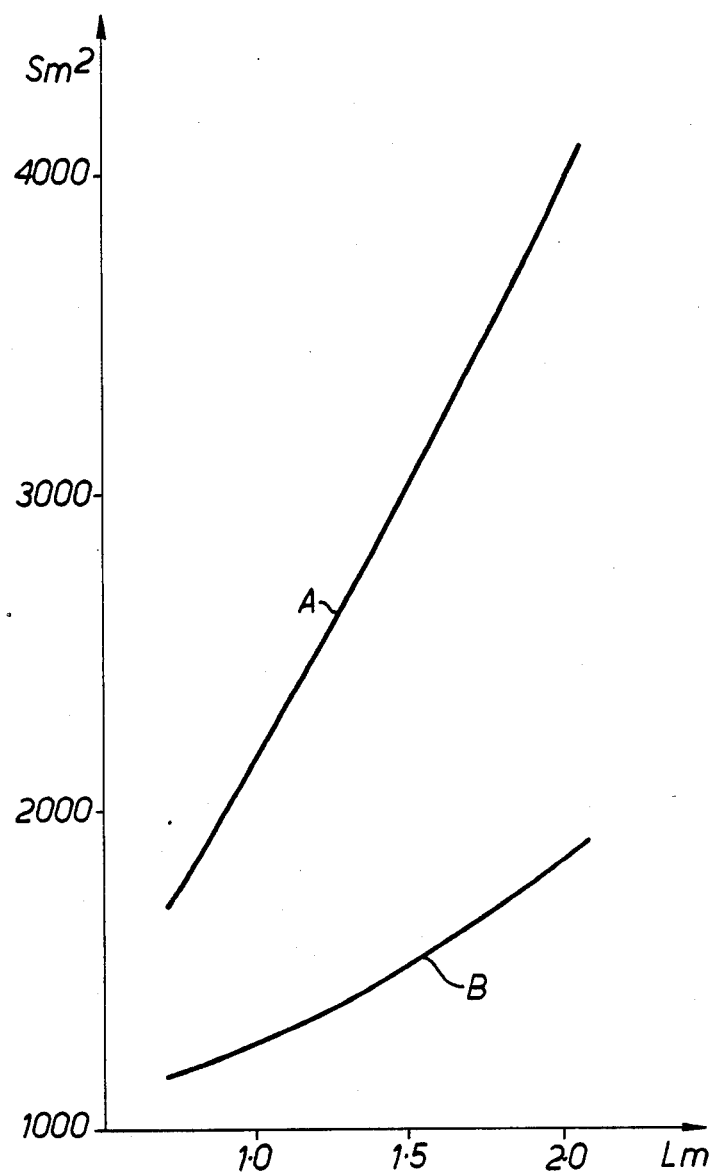
FIGS. 3 to 6 are graphs showing the variation in the membrane area required as a function of various parameters.

FIG. 3 shows the area S of membrane to be installed, plotted in $m^2$ on the ordinate, as a function of the chosen length L of fibres, plotted in meters on the abscissa, in a case A where the fibres are closed at one end and in a case B where the fibres are open at both ends, the membrane having a methane permeability of $10^{-4}$ $cm^3/cm^2.s.cm$ Hg.

Figure 4:
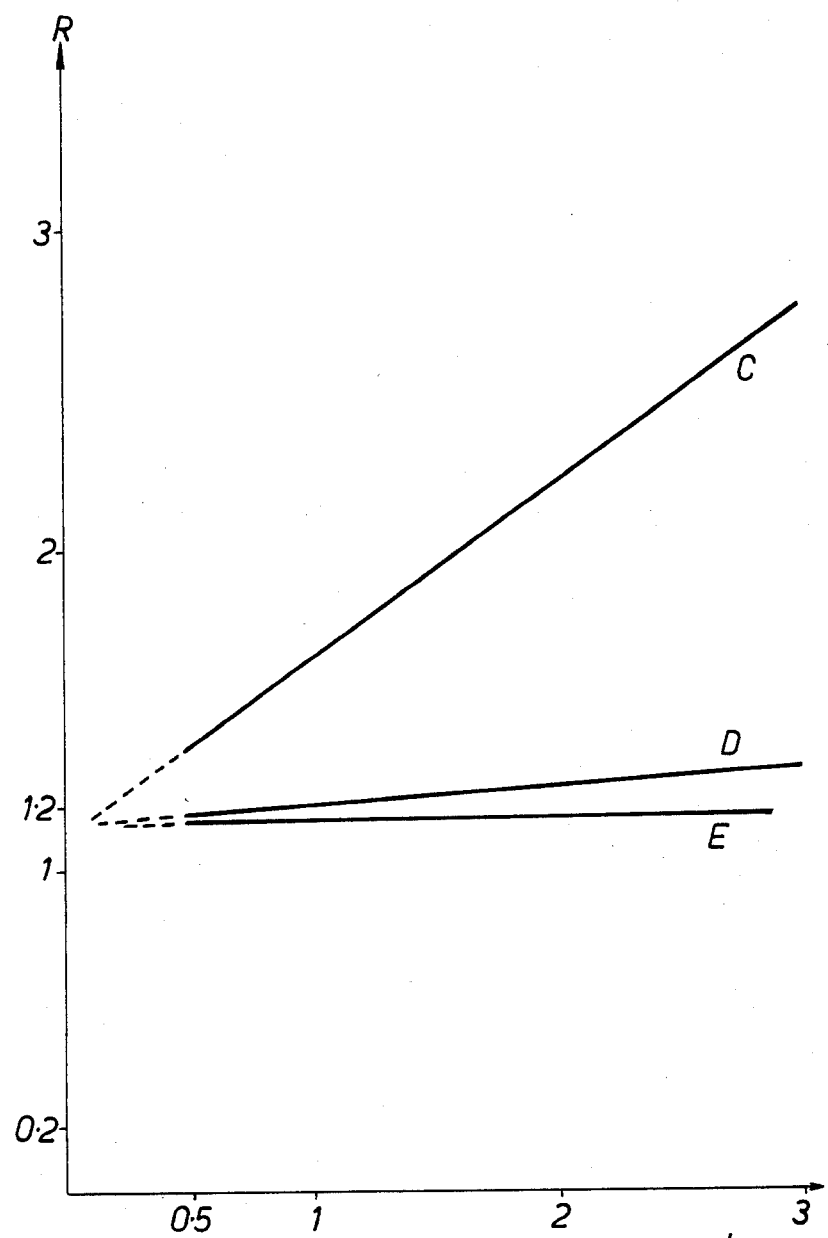

The curve B in FIG. 3 shows the great advantage of using fibres open at both ends. This advantage is only obtained, however, if the membrane is fairly permeable to methane, as shown in FIG. 4, in which the length L of the fibres has been plotted on the abscissa and the ratio R of the membrane areas required with fibres closed at one end and with fibres open at both ends, respectively, has been plotted on the ordinate. The representative curves C, D and E have been plotted for methane permeabilities of $10^{-4}$, $10^{-5}$ and $10^{-6}$ $cm^3$ $cm^2.s.cm$ Hg, respectively. It is seen that, below a permeability of $10^{-5}$, there is no longer an advantage in using fibres open at both ends, since the ratio R is of the order of 1, and that, on the contrary, the combination of a high permeability with fibres open at both ends produces an unexpected result which is particularly advantageous if the fibres have a length of more than 0.5 m, the ratio R then being considerably greater than 1.

Figure 5:
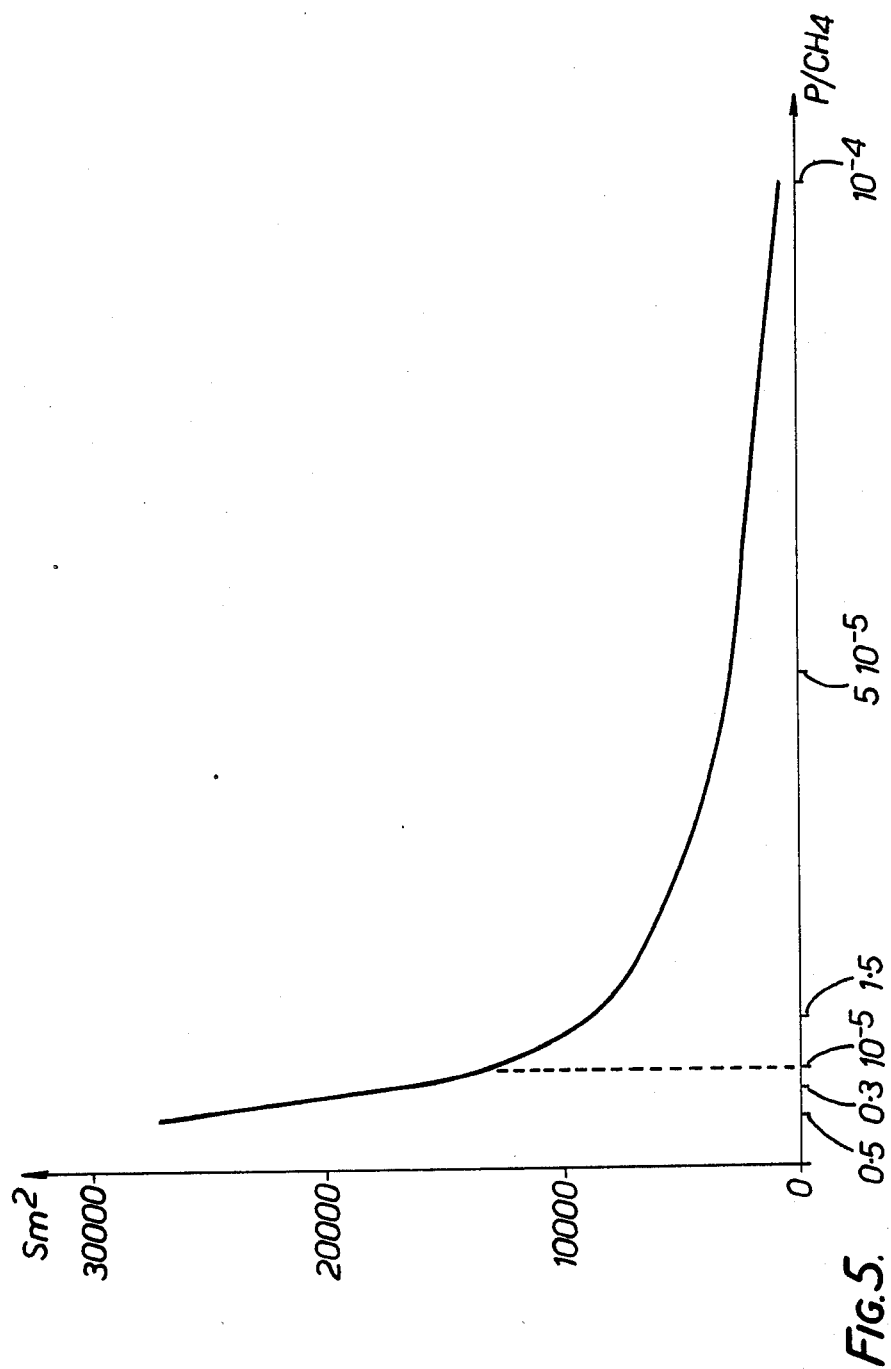

Still in the case of the previous example of gas to be treated, but with a membrane having a water/methane selectivity of 100, FIG. 5 shows the curve of the area S of membrane to be installed, plotted in $m^2$ on the ordinate, as a function of the permeability $P/CH_4$ of the membrane consisting of fibres having a length of 1 m and open at both ends, plotted on the abscissa. It is seen that a permeability $P/CH_4$ of $10^{-5}$ $cm^3/cm^2.s.cm$ Hg corresponds to a critical value below which the membrane area to be installed increases very rapidly, the tangent to the representative curve becoming almost vertical.

Figure 6:
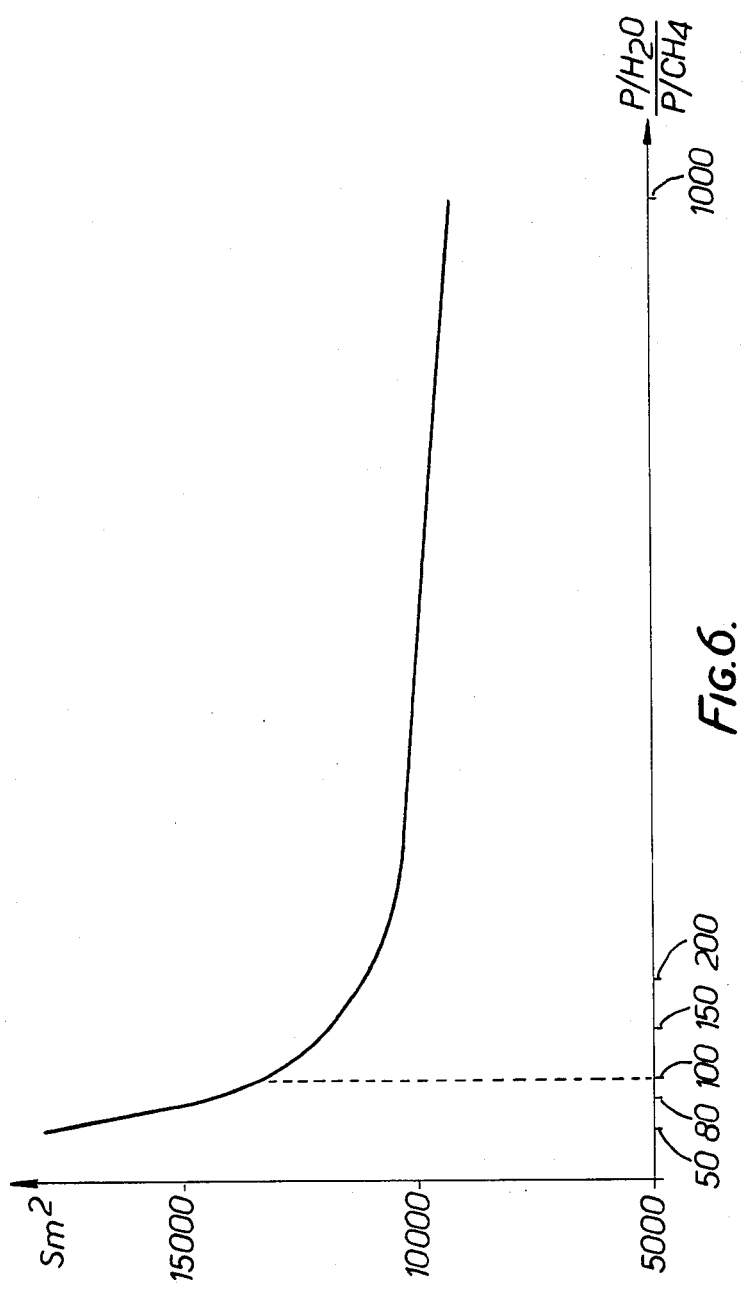

FIG. 6 shows a representative curve of the area S of membrane to be installed, plotted in m² on the ordinate, as a function of the water/methane selectivity factor of the membrane under the same conditions as in the case of FIG. 5, except that here the methane permeability was set at $10^{-5}$ cm³/cm².s.cm Hg and the selectivity was varied. It is seen that the value 100 of the selectivity factor is a critical value below which the membrane area increases very rapidly.

A comparison of the curves in FIGS. 5 and 6 shows that it would be possible to draw a three-dimensional representation of the required membrane area as a function of both the permeability and the selectivity. This representation would illustrate the critical nature of the minimum values of the methane permeability and water selectivity defined above, as is already apparent from FIGS. 5 and 6.

Figure 7:
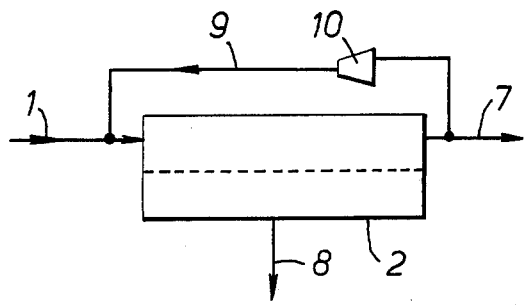
FIG. 7 is a diagrammatic view of apparatus including a permeator of FIG. 1 according to the present invention.

It happens that some membranes cannot cope with a gas to be dehydrated which is saturated with water or contains too high a concentration of water. In order to prevent water from condensing in the compartment 5, it may also be desired to reduce the water content of the gas entering the permeator 2. The scheme in FIG. 7 makes it possible to reduce this water content. To do this, a recycling line 9, equipped with a suppressor or compressor 10, connects the outlet pipe 7 to the inlet pipe 1. The suppressor 10 compensates the slight loss of pressure which the gas has undergone on flowing from the pipe 1 to the pipe 7, through the compartment 5. The gas which leaves the compartment 5 is divided into two streams, the first of which constitutes the final dehydrated gas, while the other, diverted stream is returned through the line 9 to the pipe 1, where this other gas stream mixes with the incoming gas to be dehydrated. The gaseous mixture entering the compartment 5 therefore has a water content intermediate between that of the incoming gas to be treated and that of the gas leaving the compartment 5, that is to say a content smaller than that of the incoming gas to be treated. The membrane 4 is thus protected and the performance characteristics of the separator 2 are improved.

Figure 8:
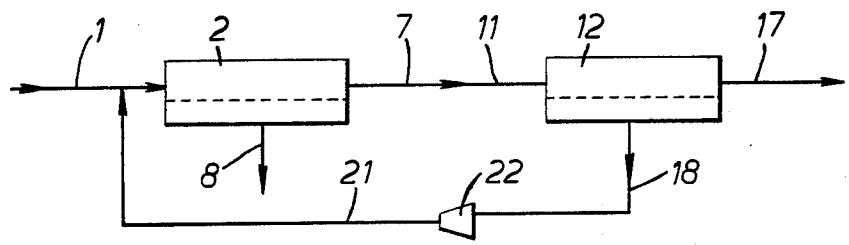
FIGS. 8 and 9 are diagrammatic installations including several stages of permeators according to the present invention.

In FIG. 8, an upstream permeator 2 is followed by a downstream permeator 12, which is of a similar type to the upstream permeator 2 and for which the same reference numbers, increased by ten, have been retained. The inlet pipe 11 entering the permeator 12 is connected to the outlet pipe 7 of the permeator 2. The dehydrated gas is recovered through the pipe 17, while the water-enriched gas leaving through the pipe 18, which has substantially the same water content as the gas arriving through the pipe 1, is returned to the inlet pipe through a line 21 fitted with a compressor 22.

Figure 9:
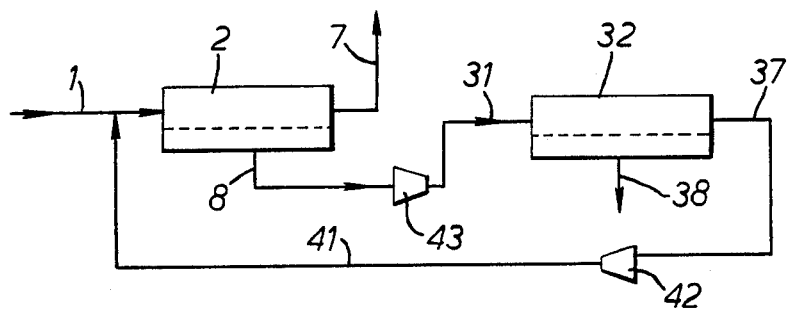

In FIG. 9, a first permeator 2 is combined with a second permeator 32, which is of a similar type to the permeator 2 and for which the same reference numbers, increased by thirty, have been retained. The dehydrated gas is taken from the pipe 7, as in the case of the diagrams in FIGS. 1 and 2, but the pipe 8 is connected to the inlet 31 of the second permeator 32, if appropriate via a compressor 43, while the outlet pipe 37 of the permeator 32 is connected to the inlet pipe 1 by a line 41 fitted with a compressor or suppressor 42.

These various permeators 12 and 32 can obviously be fitted with recycling lines similar to the line 9. Numerous other schemes of combinations of permeators in cascade can be adopted as required.

There is thus provided a process for the dehydration of a gas by permeation, which uses membranes specific for this purpose and which thus makes it possible to considerably reduce the bulk, the weight and the cost of the dehydration installation. These weight and bulk considerations are particularly important for applications on marine platforms. Even if it is envisaged both to dehydrate a gas and to adjust its contents of acid components ($CO_2$, $H_2S$), it can be preferable to use the dehydration process according to the present invention and to instal deacidification means separately, making it possible, in particular, to replace more frequently only those membranes used for dehydration, whose life can be shorter, and to have better control over the operations.

What is claimed is:

1. A process for the dehydration of a gas containing hydrocarbons, using at least one permeator which comprises a feed compartment having an inlet and a permeation compartment separated from said feed compartment by a membrane of selective permeability, and comprising supplying a gas to be dehydrated under pressure to the inlet of said feed compartment, maintaining said permeation compartment at a lower pressure than said feed compartment, withdrawing a water-enriched gas from said permeation compartment and recovering a water-impoverished gas from said feed compartment, wherein said membrane comprises a bundle of hollow fibres based on polymers, which comprise an active layer and a substrate, having an internal diameter of between 0.1 mm and 0.5 mm, a length of between 0.5 m and 3 m and a thickness of between 0.05 mm and 0.3 mm, the thickness of the active layer alone being less than 1 μm, which have a methane permeability of at least $10^{-5}$ cm³/cm².s.cm Hg and a water/methane selectivity factor of more than about 100, and which are open at both their longitudinal ends, the exterior of said hollow fibres being located in the feed compartment and the interior of said hollow fibres forming said permeation compartment.

2. A process according to claim 1, wherein the methane permeability of said membrane is of the order of $10^{-4}$ cm³/cm².s.cm Hg.

3. A process according to claim 2, wherein the water/methane selectivity factor of said membrane is between about 200 and 400.

4. A process according to claim 3, wherein the pressures and temperatures of the gases, and their water contents are monitored and regulated so as to prevent liquid water from appearing.

5. A process according to claim 3, using two said permeators which are arranged in cascade, wherein the downstream one of said permeators receives the water-impoverished gas from the upstream one of said permeators, and the water-enriched gas which leaves said downstream permeator is returned to said inlet of said upstream permeator.

6. A process according to claim 3, using a set of a first said permeator and a second said permeator, wherein said second permeator receives the water-enriched gas leaving said first permeator, and the water-impoverished gas leaving said second permeator is returned to said inlet of said first permeator.

7. A process according to claim 1, wherein the water/methane selectivity factor of said membrane is between about 200 and 400.

8. A process according to claim 1, wherein part of the water-impoverished gas recovered from said feed compartment is returned to said inlet of said feed compartment.

9. A process according to claim 1, wherein the pressures and temperatures of the gases, and their water contents are monitored and regulated so as to prevent liquid water from appearing.

10. A process according to claim 1, using two said permeators which are arranged in cascade, wherein the downstream one of said permeators receives the waer-impoverished gas from the upstream one of said permeators, and the water-enriched gas which leaves said downstream permeator is returned to said inlet of said upstream permeator.

11. A process according to claim 1, using a set of a first said permeator and a second said permeator, wherein said second permeator receives the water-enriched gas leaving said first permeator, and the water-impoverished gas leaving said second permeator is returned to said inlet of said first permeator.

* * * * *